US006280948B1

(12) United States Patent
Guilfoyle et al.

(10) Patent No.: US 6,280,948 B1
(45) Date of Patent: *Aug. 28, 2001

(54) NUCLEIC ACID INDEXING

(75) Inventors: Richard A. Guilfoyle, Germantown, MD (US); Zhen Guo, Bellevue, WA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/380,786

(22) PCT Filed: Mar. 11, 1998

(86) PCT No.: PCT/US98/04819

§ 371 Date: Sep. 3, 1999

§ 102(e) Date: Sep. 3, 1999

(87) PCT Pub. No.: WO98/40518

PCT Pub. Date: Sep. 17, 1998

Related U.S. Application Data

(63) Continuation-in-part of application No. 08/815,448, filed on Mar. 11, 1997, now Pat. No. 5,994,068.

(51) Int. Cl.$^7$ ............................. C12Q 1/68; C12Q 1/70; C12P 19/34; C07H 21/04

(52) U.S. Cl. ............................. 435/6; 435/5; 435/91.1; 536/24.3; 536/24.2

(58) Field of Search ................................ 435/6, 5, 91.1; 536/24.3, 24.2

(56) References Cited

U.S. PATENT DOCUMENTS

| 4,725,537 | 2/1988 | Fritsch et al. | 435/6 |
|---|---|---|---|
| 4,752,566 | 6/1988 | Collins et al. | 435/6 |
| 4,766,062 | 8/1988 | Diamond et al. | 435/6 |
| 5,270,185 | 12/1993 | Margolskee | 435/91.41 |
| 5,314,801 | 5/1994 | Nyez et al. | 435/6 |
| 5,348,853 | 9/1994 | Wang et al. | 435/6 |
| 5,352,580 | 10/1994 | Spears et al. | 435/6 |
| 5,389,515 | 2/1995 | Chmelo et al. | 435/6 |
| 5,445,933 | 8/1995 | Eadie et al. | 435/6 |
| 5,508,169 | 4/1996 | Deugau et al. | 435/6 |
| 5,512,458 | 4/1996 | Leonard | 435/91.1 |
| 5,552,278 | 9/1996 | Brenner | 435/6 |
| 5,599,675 | 2/1997 | Brenner | 435/6 |
| 5,700,644 | 12/1997 | Gould et al. | 435/6 |
| 5,824,481 | 10/1998 | Kambara et al. | 435/6 |
| 5,994,068 * | 11/1999 | Guilfoyle et al. | 435/6 |

FOREIGN PATENT DOCUMENTS 0 224 126 A2  11/1985  (EP).
0 450 370 A1  3/1991  (EP).

OTHER PUBLICATIONS

Boehninger Mannheim Catalog pp. 80–83 (1993).
Guilfoyle, Richard A., et al., "Ligation–mediated PCR amplification of specific fragments from a Class–II restriction endonuclease total digest," Nucleic Acids Research, 25(9): 1854–1858 (1997).
Guo, et al., Abstract entitled "Feasibility of Performing 'Restriction Hybridization Ordering'(RHO) on Glas Supports," Genome Sequencing and Analysis Conference VII, Hilton Head, SC (1995).
Hayden, et al., Abstract entitled "'Restriction Hybridization Ordering'(RHO): A Front–End Assembly Strategy for Low–Pass, High–Coverage Sequencing of Shotgun Cloned DNA," Genome Sequencing and Analysis Conference VII, Hilton Head, SC (1995).
Kalisch, Bernd W., et al., Covalently linked sequencing primer linkers (splinkers) for sequence analysis of restriction fragments (Recombinant DNA; hairpin ligation; synthetic oligodeoxynucleotides; dideoxynucleotides), Gene 44:263–270 (1986).
Liang, Peng, et al., "Analysis of Altered Gene Expression by Differential Display," Methods in Enzymology, 254:304–321(1995)/ New England Biolabs Catalog pp. 92–95 (1993).
Lisitsyn, Nikolai, et al, "Cloning the Differences Between Two Complex Genomes," Science, 259:946–951 (Feb. 12, 1993).
Lisitsyn, Nikolai, et al., "Representational Difference Analysis in Detection of Genetic Lesions in Cancer," Methods in Enzymology, 254:291–303 (1995).
Perucho, Manuel, et al., "Fingerprinting of DNA and RNA by Arbitrarily Primed Polymerase Chain Reaction: Applications in Cancer Research," Methods in Enzymology, 254:275–290 (1995).
Quartin, Robin S., et al., "Branch Migration Mediated DNA Labeling and Cloning," Biochemistry, 28:8676–8682 (1989).
Rosenberg, Michael, "RFLP subtraction"; A method for marking libraries of polymorphic makers, Proc. Natl. Acad. Sci. USA, 92:6113–6117 (6/94).
Smith, Douglas R., "Ligation–mediated PCR of Restriction Fragments from Large DNA Molecules," PCR Methods and Applications, 2:21–27 (1992).

(List continued on next page.)

*Primary Examiner*—John S. Brusca
*Assistant Examiner*—Stephen Siu
(74) *Attorney, Agent, or Firm*—Quarles & Brady LLP

(57) ABSTRACT

A restriction site indexing method for selectively amplifying any fragment generated by a Class II restriction enzyme includes adaptors specific to fragment ends containing adaptor indexing sequences complementary to fragment indexing sequences near the termini of fragments generated by Class II enzyme cleavage A method for combinatorial indexing facilitates amplification of restriction fragments whose sequence is not known. Profiling methods and other methods for characterizing polynucleotides are presented.

29 Claims, 5 Drawing Sheets

OTHER PUBLICATIONS

Stratagene Catalog pp. 140–142 (1993).

Unrau, Paul, et al., "Non–cloning amplification of specific DNA fragments from whole genomic DNA digests using DNA 'indexers'," Gene, 145:163–169 (1994).

Vos, Pieter, et al., "AFLP: a new technique for DNA fingerprinting," Nucleic Acids Research, 23(21):4407–4414 (1995).

Weinstock, Peter H., et al., "Branch capture reactions: effect of recipient structure," Nucleic Acids Research, 18(14):42074213 (1990).

Wong, Daphne M., et al., "Branch capture reactions: displacers derived from asymmetric PCR," Nucleic Acids Research, 19(9):22512259 (1991).

Zheleznaya, L.A., et al., A Method for Selective PCR–Amplification of Genomic DNA Fragments (SAGF Method), Biochemistry (Moscow), 60:1037–1043.

* cited by examiner

A. *END-SPECIFIC ADAPTORS*

LEFT w/forward primer

| -21M13 | 5' | tgtaaaacgacggccagt |
|---|---|---|
| 517L | 3' | ACATTTTGCTGCCGGTCA<u>CTAGT</u>GGTC |
| 560L |  | ACATTTTGCTGCCGGTCA<u>CTAGT</u>GGTA |
| 1567L |  | ACATTTTGCTGCCGGTCA<u>CTAGT</u>GATA |
| 2684L |  | ACATTTTGCTGCCGGTCA<u>CTAGT</u>AGTC |
| 4459L |  | ACATTTTGCTGCCGGTCA<u>CTAGT</u>GGGC |
| 4623L |  | ACATTTTGCTGCCGGTCA<u>CTAGT</u>CAAG |
| 6330L |  | ACATTTTGCTGCCGGTCA<u>CTAGT</u>CAAA |
| 18909L |  | ACATTTTGCTGCCGGTCA<u>CTAGT</u>CGGC |

RIGHT w/reverse primer

| M13RevP | 5' | caggaaacagctatgacc |
|---|---|---|
| 517R | 3' | GTCCTTTGTCGATACTGG<u>CTAGT</u>GAAG |
| 1576R |  | GTCCTTTGTCGATACTGG<u>CTAGT</u>CAGT |
| 2684R |  | GTCCTTTGTCGATACTGG<u>CTAGT</u>CGGA |
| 4459R |  | GTCCTTTGTCGATACTGG<u>CTAGT</u>GGAG |
| 4623R |  | GTCCTTTGTCGATACTGG<u>CTAGT</u>TCCT |
| 6330R |  | GTCCTTTGTCGATACTGG<u>CTAGT</u>TGAC |
| 8848R |  | GTCCTTTGTCGATACTGG<u>CTAGT</u>TTAG |
| 18909R |  | GTCCTTTGTCGATACTGG<u>CTAGT</u>GGTG |

B. *COMBINATORIAL ADAPTORS w/forward or reverse primer*

| Combo-FP | 5' | tgtaaaacgacggccagt |
|---|---|---|
|  | 3' | ACATTTTGCTGCCGGTCA<u>CTAGT</u>NNNN |
| Combo-RP | 5' | caggaaacagctatgacc |
|  | 3' | GTCCTTTGTCGATACTGG<u>CTAGT</u>NNNN |

FIG 3

DpnII adaptors w/forward primer

```
5'    tgtaaaacgacggccagt
3'    ACATTTTGCTGCCGGTCACTAGGACC
      ACATTTTGCTGCCGGTCACTAGCGAC
      ACATTTTGCTGCCGGTCACTAGCCGA
      ACATTTTGCTGCCGGTCACTAGGAGA
```

NlaIII adaptor w/reverse primer

```
5'    CAGGAAACAGCTATGACCCATG
3'    GTCCTTTGTCGATACTGG
```

FIG 4

Sau3AI: 5' ▾GATC
            CTAG▴ tgtaaaacgacggccagt         +          GATCTTTT------ IL-2
ACATTTTGCTGCCGGTCACTAGAAAA            AAAA------

↓ T4 DNA Ligase

M13 forward →
tgtaaaacgacggccagtGATCTTTT--------//----⎡────┬────⎤
ACATTTTGCTGCCGGTCACTAGAAAA ┌-------//----⎣────┴────⎦
                           A              ← N₁N₂(dt)₁₈  heel
                           A                (AT)
                           A
                           A 3'

200    =    26      +     142 (-8)    +    40

Sau3AI indexing adaptors:

tgtaaaacgacggccagt
ACATTTTGCTGCCGGTCACTAGGACC       IS-1
                      CGAC       IS-2
                      CCGA       IS-3
                      GAGA       IS-4
                      GACT       IS-5
                      AGTC       IS-6
                      TATA       IS-7
                      ATAT       IS-8
                      AAAA       IS-9 (IL-2)

FIG 5

NUCLEIC ACID INDEXING

CROSS-REFERENCE TO RELATED APPLICATIONS

This application is a continuation-in-part application of U.S. application Ser. No. 08/815,448, filed Mar. 11, 1997 which is incorporated herein by reference in its entirety.

BACKGROUND OF THE INVENTION

It is known in the art of molecular biology that a nucleic acid fragment lying between two identified and unique primer sequences can be amplified using the polymerase chain reaction (PCR) or modifications of the PCR. PCR avoids conventional molecular cloning techniques that require the existence in nucleic acid of advantageous restriction endonuclease cleavage sites. One identified shortcoming of PCR is that fragments greater than about 40 kilobase pairs between the PCR primers are only weakly amplified. It has been difficult to obtain meaningful sequence data from large genomic fragments, particularly when such fragments are resistant to traditional cloning methods. Thus, the art is seeking new methods to obtain the nucleic acid sequences of long, uncharacterized regions of genetic material.

Efforts to amplify a specific DNA cleavage fragment from a population of such fragments have included methods that involve cleaving the DNA using Class IIS enzymes or interrupted palindrome enzymes to form fragments having non-specific terminal 5' or 3' overhangs of various lengths (generally 2 to 5 bases). Smith, D. R., PCR Methods and Applications 2:21–27, Cold Spring Harbor Laboratory Press (1992); Unrau, P. and K. Deugau, Gene 145:163–169 (1994); U.S. Pat. No. 5,508,169 (Deugau et al.); Zheleznaya, L. A. et al., Biochemistry (Moscow) 60:1037–1043 (1995). Class IIS enzymes cleave DNA asymmetrically at precise distances from their recognition sequences. Interrupted palindrome ("IP") enzymes cleave symmetrically between a pair of interrupted palindromic binding sites. To amplify the products of such cleavages, nucleic acid indexing linkers, containing protruding single strands complementary to the cohesive ends of Class IIS- or IP cleavage sites (rather than recognition sequences) and PCR primer sites, have been annealed and ligated to fragments generated by Class IIS- or IP cleavage.

The overhangs vary in base composition, and are determined by the locations of the enzymes' cleavage sites in a genome. The base composition and sequence of the overhang created after cleavage with a Class IIS or IP enzyme cannot be predicted because the sites at which those enzymes cleave DNA are determined by spatial relationship to the recognition sequence, but are not sequence-determined. In the methods described by Smith, Unrau, Deugau and Zheleznaya, the unique cleavage sites generated by Class IIS and IP enzymes determined a random sequence by which fragments could be indexed. However, that is not the case with more popular Class II enzymes that cleave within their recognition sites and generate predictable, identical sticky ends on each restriction fragment. Also, Unrauls method employs temperatures that result in a problem of illegitimate base pairing as well as problems with primer dimers, where indexing fragments anneal with one another rather with the target DNA.

What is desired is an indexing system that relies upon fragments not generated by Class IIS or IP enzymes, and which offer improved amplification specificity.

BRIEF SUMMARY OF THE INVENTION

The present invention is summarized in that oligonucleotide adaptors for directing PCR amplification can be engineered to efficiently and selectively hybridize "fragment indexing sequences" of one or more bases immediately adjacent to a Class II restriction enzyme recognition sites at the termini of a nucleic acid fragment. A Class II enzyme cleaves nucleic acid within its recognition site to generate a characteristic 5' or 3' overhanging end or blunt end. The recognition site can include one or more bases that do not form part of the end that results from enzymatic cleavage. When the adaptor and the nucleic acid fragment are brought together under conditions suitable for intra-strand hybridization, the invading strand of the adaptor displaces a portion of the nucleic acid fragment.

Each oligonucleotide adaptor comprises a duplex portion and a single-stranded portion. The duplex portion comprises an invading strand and a complementary PCR primer strand hybridized to the invading (displacing) strand. The oligonucleotide adaptors for the two termini are distinct, in that the PCR primer strands (and their complements on the invading strand) of each end adaptor are selected to specifically amplify fragments in the forward or reverse direction. The PCR primer strand, which contains the sequence that is the same as that used for a PCR primer, provides a 3'-OH group that is required to join the adaptor to the restriction fragment in the method. The invading strand, which is longer than the PCR primer strand, also includes a protruding single-stranded portion that comprises (1) a nucleic acid sequence that can hybridize to the characteristic overhang and (2) an adaptor indexing sequence that is perfectly complementary to the fragment indexing sequence. The adaptor indexing sequence is provided at the 5' end of the single-stranded portion of the invading strand.

The invention is further summarized in that oligonucleotide adaptors of the type described can be used in a method for amplifying a restriction fragment that includes the steps of:

(a) cleaving linear of circular nucleic acid at a restriction enzyme recognition site with at least one rare-cutting Class II restriction enzyme to generate a linear restriction fragment having a characteristic 5' or 3' overhang at each fragment terminus;

(b) hybridizing to each terminus of the fragment an end-specific oligonucleotide adaptor, thereby displacing one strand of the fragment;

(c) enzymatically ligating the restriction fragment to the primer strand to form a strand-displaced structure; and (d) amplifying the strand-displaced structure.

The invention is further summarized in that a combinatorial degenerate mixture of oligonucleotide adaptors comprising every indexing sequence is also useful in a method for combinatorial indexing.

In a related aspect, the invention is summarized in that in a method for combinatorial indexing, genetic material cleaved with a rare-cutting enzyme produces a set of fragments for subsequent amplification. The cleaved DNA is added into an array of separate amplification reactions, where each reaction contains both an adaptor specific for one fragment indexing sequence and the degenerate combinatorial mixture of all indexing adaptors specific to the other end of the fragment. Undesired complexity in reaction processing is avoided by including both the single end-specific adaptor and the combinatorial array of adaptors in the hybridization step.

In addition to obtaining valuable sequence data from the amplified fragments, it is possible to order the fragments by generating a restriction map by performing cross-digestion using two or more different enzyme arrays. By selecting the adaptor sequence, various PCR-related methods can be employed directly on the amplification products, including PCR sequencing.

The invention is further summarized in that the adaptors are advantageously employed in methods for indexing, profiling, and characterizing polynucleotides. Adaptors can be grouped into desirable groups to acquire and analyze data gathered in the indexing, profiling and characterizing methods.

It is an object of the present invention to facilitate genetic profiling.

It is another object of the present invention to facilitate accessing and sequencing regions of the human genome that are resistant to molecular cloning.

It is yet another object of the present invention to amplify nucleic acid fragments with specificity.

It is a feature of the present invention that the overhang generated by cleavage with a Class II enzyme is predictable and invariant for each enzyme.

It is another feature of the present invention that the indexing sequence is separate from (not a part of) the overhang generated by restriction enzyme cleavage.

It is yet another feature of the present invention that a degenerate collection of adaptors containing all possible indexing sequences is used in combination with a defined adaptor duplex to amplify unknown sequences of enzyme-cleaved nucleic acid.

It is an advantage of the present invention that the methods rely upon Class II enzymes rather than the less common Class IIS and IP enzymes.

It is another advantage of the present invention that the hybridizing regions of the fragments and adaptors are longer than have been used in previous indexing systems.

Another advantage of the present method is the remarkable specificity with which adaptors anneal to restriction fragments when there is perfect matching between the bases of the indexing sequence and the complementary basis of the restriction fragment.

A fully automated PCR adaptor array strategy could bypass conventional cloning by simultaneously generating a restriction map and DNA fragments for subcloning or direct sequencing from 0.5 Mb in about one day while avoiding problems associated with so-called unclonable regions. If large DNA pieces are to be mapped and sequenced, the DNA (up to about 0.5 Mb) must be purified using an existing technology such as site-specific excision (RARE, achilles heel, PNA) or RARE-cutter restriction endonucleases (e.g., NotI or meganucleases (intron-encoded endonucleases)).

It is also possible to combine the method with conventional PCR, or to use the method in a process for chromosome walking from the ends of fragments using indexers determined while preparing a restriction map.

Another application for the method is in genetic mapping to amplify fragments generated in restriction fragment length polymorphism (RFLP) analysis. Amplified fragments created from such fragments would be sequence-ready and could be used directly as probes in genetic mapping. It may also be advantageous to first perform representational difference analysis (RDA) (Lisitsyn, N. et al. *Science* 259:946–951 (1993)) or RFLP-subtraction (Rosenberg, M. et al., *PNAS USA* 91:6113–6117 (1994)) to reduce the complexity.

The method could also be used as an alternative to AFLP (Vos, P. et al., *N. A. R.* 21:4407–4414 (1995)) or arbitrarily-primed-PCR for analyzing altered gene expression by differential display (Perucho, M. et al., *Methods in Enzymology* 254:275 (1995); Liang, *Methods in Enzymology* 254:304 (1995). This method would have advantages over AP-PCR such as reduced noise and cleaner probes for gene hunting, better detection of rare messages, and a requirement for a smaller number of oligonucleotides.

Other objects, advantages, and features of the present invention will become apparent upon consideration of the following detailed description taken in conjunction with the drawings.

BRIEF DESCRIPTION OF THE SEVERAL VIEWS OF THE DRAWINGS

FIG. 3A depicts the end-specific adaptors used in the preferred embodiment to amplify the internal BclI fragments of λ DNA. The illustrated left end-specific adaptors include a –21 MI 3 primer strand (SEQ ID NO:1) and one of several possible invader strands (SEQ ID NO:2 through SEQ ID NO:9). The illustrated right end-specific adaptors include an M13RevP primer strand (SEQ ID NO:10) and one of several possible invader strands (SEQ ID NO:11 through SEQ ID NO:18).

FIG. 3B shows the degenerate set of combinatorial adaptors used in the preferred embodiment to provide a proof of concept of the invention. The illustrated Combo-FP adaptor includes a –21 M13 primer strand (SEQ ID NO:1) and one possible invader strand (SEQ ID NO:19), and the illustrated Combo-RP adaptor includes an M13RevP primer strand (SEQ ID NO:10) and another possible invader strand (SEQ ID NO:20).

FIG. 4 shows the end-specific adaptors used in a method for differential display of cDNAs in accordance with the present invention. The illustrated DpnII adaptors include a –21M13 primer strand (SEQ ID NO:1) and one of several possible invader strands (SEQ ID NO:23 through SEQ ID NO:26), and the illustrated NlaIII adaptor includes a reverse primer strand (SEQ ID NO:28) and one possible invader strand (SEQ ID NO:27).

FIG. 5 shows a strategy for amplifying 3' ends of mRNA (cDNA) using adaptors of the present invention. The illustrated Sau3AI indexing adaptors include a –21 M13 primer strand (SEQ ID NO:1) and one of several possible invader strands (SEQ ID NO:23 through SEQ ID NO:26 and SEQ ID NO:33 through SEQ ID NO:37, respectively from top to bottom).

DETAILED DESCRIPTION OF THE INVENTION

Figure 1:
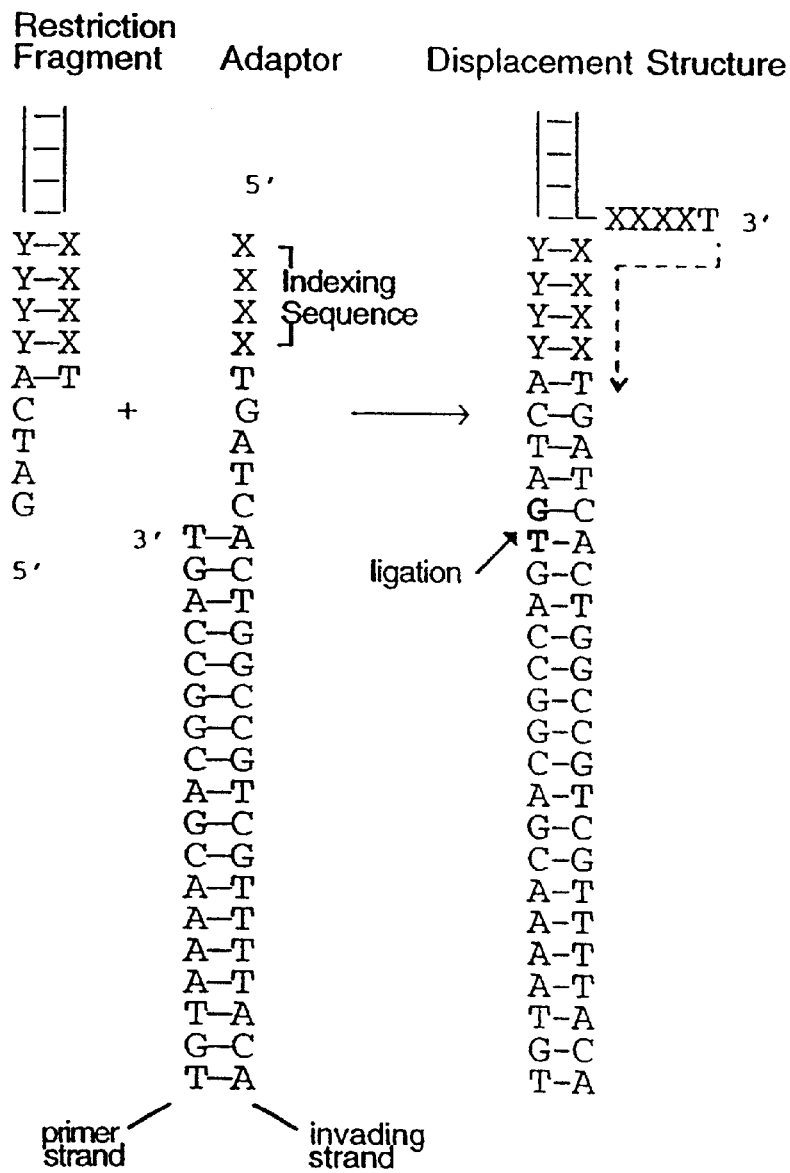
FIG. 1 shows an embodiment of the restriction site indexing method of the present invention. The figure depicts one end of a restriction fragment generated by cleavage with a Class II enzyme that generates a defined 5' overhang, a partially single stranded adaptor duplex having a primer strand (SEQ ID NO:1) and an invader strand (SEQ ID NO:19), and the displacement structure (SEQ ID NO:19 and nucleotides complementary to SEQ ID NO:19) formed by hybridization and ligation of the fragment and the adaptor.
Figure 2:
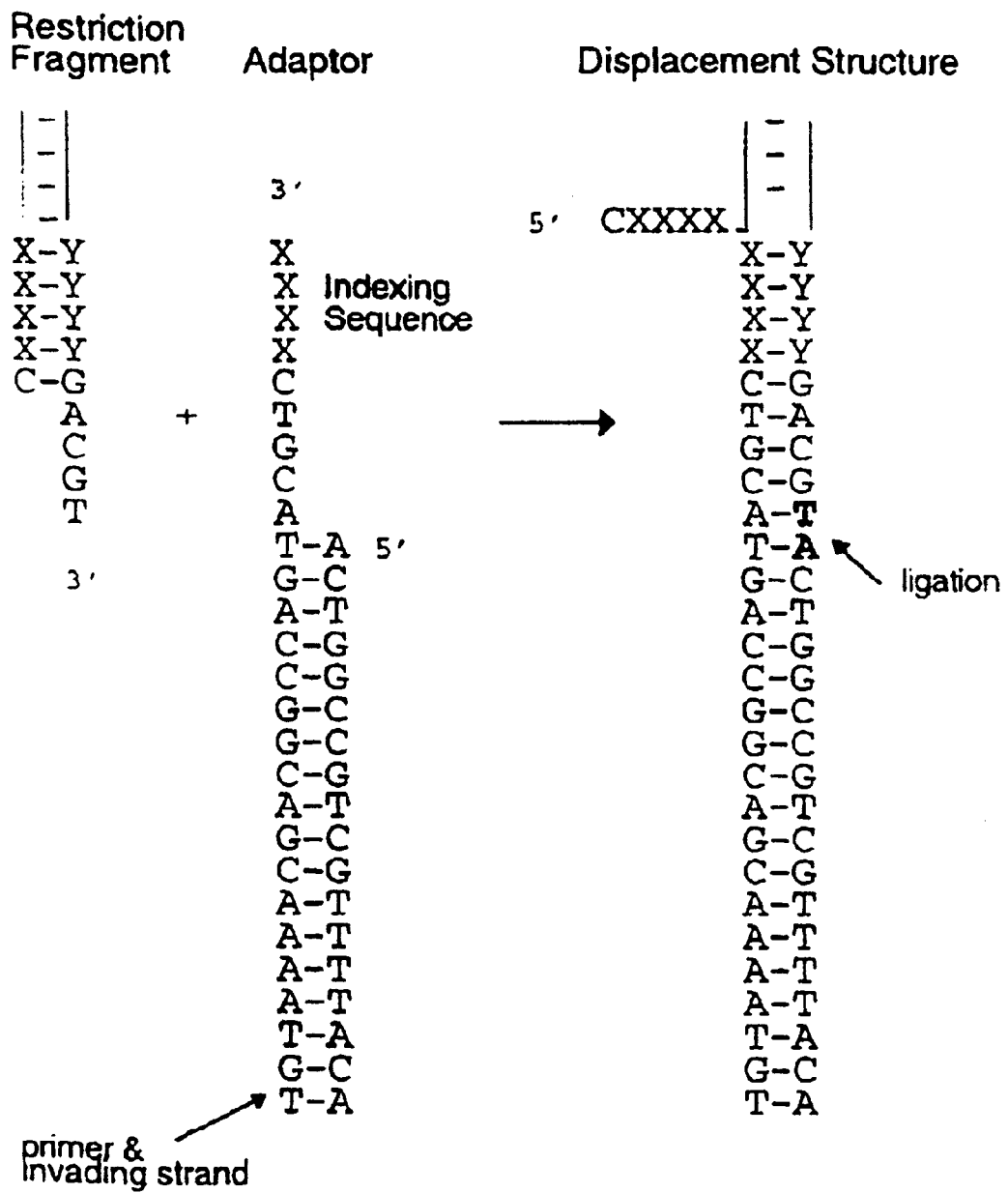
FIG. 2 shows a schematic embodiment of the invention where the restriction fragment generates a defined 3' overhang for ligation with a partially single stranded adaptor duplex having a primer strand (SEQ ID NO:30) and an invader strand (SEQ ID NO:29) to form the displacement structure (SEQ ID NO:29 and nucleotides complementary to SEQ ID NO:29).

Reference is made to FIG. 1 which illustrates an embodiment of the restriction site indexing method of the present invention. In FIG. 1, a restriction fragment generated by cleavage with a Class II enzyme generates a defined 5' overhang (see left side of FIG. 1). In FIG. 2 (SEQ ID NO:29 through SEQ ID NO:31), a restriction fragment generated by cleavage with a Class II enzyme generates a defined 3' overhang (see left side of FIG. 2). When the enzyme generates a 3' overhang, the longer strand can act as both invading strand and primer strand. For example, in FIG. 2, the M13 forward primer (TGTAAAACGACGGCCAGT) (see also, SEQ ID NO:1) is the first 18 bases of the longer strand. The 18-mer primer oligonucleotide needs to be added for PCR amplification. No fill-in of the adaptor is required, as it is in the 5'-overhang case. Except as noted herein, the invention functions in the same manner when the enzyme generates a 3' overhang.

In the convention of this patent application, "forward" primers are specific for the "left" end of a fragment; "reverse" primers are specific for the "right" end of a fragment, where the fragment is presented with the 5'→3' strand as the top strand. As noted, a unique primer can be provided for all adaptors, if 2-strand sequencing is not desired.

Each fragment generated by cleavage of nucleic acid with a Class II restriction enzyme can be defined by a pair of fragment indexing sequences, defined as the one or more bases adjacent to the terminal recognition sites of a Class II restriction enzyme used to generate the fragment. Accordingly, a unique pair of indexing adaptors, having the partially-singled stranded structures described herein, can hybridize to the two termini of a fragment.

Even though the characteristic overhangs at the termini are identical, the fragment indexing sequences adjacent to the recognition site are not predictable; any combination of bases can reside at the indexing positions. It is noted that, because of an enzyme's cleavage strategy, one or more base pairs of the complete recognition site (e.g., in the exemplified embodiment of FIG. 1, an A-T pair) can remain near the fragment terminus and should be accommodated during adaptor design.

Adjacent to the enzyme recognition site are the bases of the fragment indexing sequence, shown in FIG. 1 as X, which can be, but need not be, identical bases. In the fragment, Y represents the base complementary to X at a given position. Thus, if X is A, Y can be T; if X is G, Y can be C; if X is C, Y can be G, and if X is T, Y can be A. Other recognized non-natural base pairs can also form. Because the fragment indexing sequence is not a part of the recognition or cleavage sequence per se, neither the indexing sequence, nor its length, are limited by the choice of enzyme. This is an advantage over ligation-mediated indexing systems known in the art.

The chance that any one indexing sequence will correspond to more than one terminus decreases as the indexing sequence length increases. Accordingly, it is desirable to select a preferred indexing sequence length. The suitable size of the fragment indexing sequence will depend upon the application to which the method is put. If the goal is specific fragment amplification, greater specificity is desired so the indexing sequence should preferably be 3, 4, or 5 bases long. However, fragment fingerprinting or differential display of cDNAs can be accomplished using a preferable indexing sequence length of 1, 2, or 3 bases. An upper limit of 10 bases in the indexing sequence is contemplated.

By way of example only, the case of preparing adaptors for amplifying a fragment is considered. There are 64 3-base-long indexing sequences, 256 4-base-long indexing sequences, and 1024 5-base-long indexing sequences. A 4-base-long indexing sequence (256 choices) is preferred. Three- or five-base-long indexing sequences could possibly be used, although if a shorter sequence were used, the selectivity would be compromised (in the sense that more fragments would be amplified per adaptor pair), and if a longer sequence were employed, sample handling becomes increasingly difficult because of the array size.

It is also desirable to select a preferred nucleic acid cleavage frequency. If many fragments are generated, the likelihood that more than one fragment will be recognized by identical adaptor pairs increases. One of ordinary skill will appreciate that the desired number of fragments will depend upon the application to which the method is put. If few fragments are generated, PCR amplification of longer fragments (with the accompanying art-recognized difficulties) will be required.

Thus a rare-cutting enzyme is preferred. In methods for restriction mapping or DNA fingerprinting, and for complex genomes, the preferred restriction enzyme used to cleave the target DNA is a 6-cutter. Five-cutters could be used, except that they are few in number and recognize degenerate sequences, thereby adding to the complexity of the required adaptors. Four-cutters are thought to be unsuitable because of their abundant distribution of cleavage sites. Enzymes cutting at sites of greater than 6 bases are also believed to be unfeasible, given their extreme rarity in the genome. On the other hand, for genomes of lower complexity, or for RNA fingerprinting (using cDNA targets) and differential display applications, 4-cutter enzymes would be suitable. Combinations of enzymes having different cleavage frequencies can be well suited for generating fragments having a certain desired average size, or for a particular target sequence.

A simple calculation for 6-cutters predicts that 256 individual, sequence-ready restriction fragments can be amplified from a target DNA of up to 0.5 megabases (Mb) in size. DNA of 1 Mb complexity digested with a 6-cutter enzyme, which cleaves a random sequence on average every 4096 base pairs, will produce 244 fragments, on average. Dividing this by 256 indexers yields about 1 amplified fragment per end-specific adaptor/combinatorial adaptor pair used. An indexing sequence would be present twice in the full library (array) of adaptors, with one contributed by the end-specific adaptor and the seconds by the combinatorial adaptor. A fragment would be amplified twice, but at different locations in the array, and therefore a 0.5 Mb target DNA segment would be accommodated bidirectionally for isolating individually amplified restriction fragments. If the target DNA is greater than 0.5 Mb, the method is still applicable using either complete digests or partial random digests such that more than one restriction fragment may be amplified per well.

The above-noted combination furnishes the convenience of easy to automate arrays of 256 members and a distribution of restriction sites that yields amplification lengths compatible with state-of-the-art PCR amplification technology.

The center of FIG. 1 shows an indexing adaptor of the type described. Indexing adaptors contain a region for PCR priming (or other function), a region complementary to a Class II restriction enzyme recognition site, and a strand-displacement region which is complementary to the fragment indexing sequence adjacent to the recognition site on the overhang strand.

Although it is referred to herein for convenience as the PCR primer strand, the strand can comprise any sequence that is desired to be placed at a terminus of a fragment having the specified indexing sequence and can provide any desired function, for example, a restriction enzyme recognition/cleavage site, to facilitate subsequent processing of amplified fragments. Thus, the adaptors of the present invention have appreciably broader utility than for PCR amplification. If the function to be provided by the adaptor is PCR amplification, then the sequence should be unique or present in low copy number, should provide an available 3' end and should be recognized by a suitable polymerase enzyme, such as Taq or TthI polymerase. The −21M13 forward primer or the M13revP reverse primer (together, "the M13 primers") are suitable primers if the amplified fragments will be used for subsequent bi-directional sequencing. The −21M13 and M13revP primers are specific for the left and right ends of a restriction fragment, as those terms are used herein. The M13 primers, used as described herein, permit amplified fragments to be sequenced on both strands. If bidirectional sequencing is not desired, distinct primers need not be provided. For terminal fragments of linear nucleic acid molecules, a suitable amplicon-specific terminal primer can be provided in place of an adaptor if the terminal sequence is known. The sequences for amplifying the fragment can also be sequences for elongation of a template by a DNA or RNA polymerase, such as a T3 promoter, a T7 promoter, an SP6 promoter, or a sequence complementary to same.

The invading strand includes a portion complementary to the primer strand. Also, adjacent to that portion is a sequence that can hybridize to the Class II enzyme recognition site of the fragment terminus (including any residual bases near the fragment terminus that do not form part of the overhang) to form the displacement structure shown at the right in FIG. 1. Note that although a second displacement structure, wherein the indexing sequence is displaced by the restriction fragment, could form, it is not favored and is not observed, for it results in a net loss of 5 nucleotides available for annealing by the invading strand.

Strand-displaced structures of this type are described in EP-A-0 450 370 A1, Quartin et al., Biochemistry 28:8676–8682 (1989), Weinstock and Wetmur, Nucleic Acids Res. 18:4207–4213 (1990), and Wong et al., Nucleic Acids Res. 19:2251–2259 (1991), which are incorporated herein by reference in their entirety, most particularly the parts relating to the formation, structure and properties of strand-displaced structures useful in the present invention.

The above-noted documents describe Branch Capture Reactions ("BCR") that involve sequence-dependent attachment of a single-stranded tail to a duplex DNA, in which one strand of the duplex is displaced by the single-stranded tail. The strand-displaced structure formed in BCR is akin to that of the present invention, and the parameters of formations described in the publications may be used in carrying out indexing methods of the present invention. However, the documents are directed to capturing specific, individual DNA fragments from a mixture using unique sequences rather than a mixture of indexing sequences, and concern direct cloning of the captured fragments rather than indexing analysis of polynucleotides in a mixture.

The documents also relate that formation of strand-displaced structures and capture of specific fragments can be facilitated by incorporating duplex-stabilizing modified bases in the capture tail. The present invention can be carried out without using modified bases in the adaptor single-stranded indexing region. Nevertheless, modified bases can be employed in the present invention to stabilize duplexes formed between an indexing adaptor and a polynucleotide to be indexed. In some circumstances, it may prove particularly advantageous to do so. Among the modified bases of this type are pyrimidines substituted with bromine at C5, particularly C5-substituted BrdC (5-bromodeoxycytidine). Also useful in this regard are 5-methyl substituted pyrimidines, particularly 5-methyldeoxycytidine.

DNA ligase efficiently joins the adaptor to the restriction fragment only if the adaptor indexing sequence is perfectly complementary to the corresponding fragment indexing sequence. Even one mismatched base in the adaptor indexing sequence will discourage efficient ligation and subsequent PCR amplification relative to a perfectly matched adaptor.

However, the hybridizing portion need not be completely complementary to the overhang, in the sense of classic Watson-Crick base pairing. A universal mismatch base analog (such as 3-nitropyrrole) could be positioned within the restriction site to elicit an effect on the indexing sequence moiety. Moreover, a string of such base analogs could be used to completely replace every base within the restriction site, so that all four indexer bases could experience enhanced discrimination and a universal adaptor could be developed for most 6-cutter restriction enzymes. This would require that the base analog or analogs incorporated not greatly affect ligase activity.

By positioning a universal base mismatch in 3 to 4 base proximity to a natural base mismatch, the $T_m$ is lowered by up to 8° C. relative to a perfect match. This discrimination enables one to amplify only fragments that perfectly match the indexing sequence provided from a digest containing many fragments. Although this can lower overall duplex stability by as much as 15° C., the enhanced discrimination would be significant for the indexing sequences. This is because discrimination is generally reduced at natural base mismatches near 3' ends, for example, where the indexer sequences are located in the adaptor oligonucleotides.

Both positional and compositional differences may have an effect upon hybridization efficiency. It is anticipated that differences in discrimination by adaptors for indexing sequences may relate to GC content, illegitimate base pairing issues, proximity to the site of ligase joining, and contiguous base stacking effects.

One or more natural base analogs (such as 5-nitroindole) can also be added to the overhanging 5' end of an adaptor, if desired, to center the indexing sequence in the hybridizing portion thereby further enhance discrimination between exact and mismatched indexing sequences. The number of such bases that can be added can be as long as the number of bases in the portion of the invading strand that is complementary to the restriction recognition sequence.

Improved discrimination is most apparent when the universal mismatch nucleotide is provided in either of the first two positions adjacent to the indexing sequence unless the position is itself adjacent to a mismatch, which causes reduced stability. When the universal mismatch is provided any closer than three bases from the site at which subsequent ligation occurs, it is thought that the non-natural base interferes with ligation efficiency and less amplified product is produced relative to that amount produced after combining the adaptor having a perfectly matched indexing sequence.

The indexing adaptor can be formed by hybridizing a primer strand and an invading strand together under standard annealing conditions. A primer strand and an invading strand can be synthesized separately using oligonucleotide synthesis methods that are conventional in the art. Many oligonucleotide primers for use as primer strands are readily commercially available. The M13 primers are commercially available, are in widespread use, and can be fluorescently tagged. In addition, the M13 primers have annealing temperatures that are very close to one another. This property is desirable in that both the forward and reverse amplifications can proceed with comparable efficiency under a single set of conditions. As noted, the two sequencing primers need not be used if direct sequencing is not desired.

The invention can be embodied in a method for amplifying fragments of known sequence, using readily engineered adaptors having suitable adaptor indexing sequences specific for both ends of the known fragment. Also, by providing combinatorial mixtures comprising all possible adaptors specific to the fragment ends, one can amplify any fragment without knowing the identity of the indexing sequence specific for either terminus. The invention can also be practiced on a fragment where one end is known but the other end is unknown, by employing in the method one end-specific adaptor or amplicon-specific primer for the known fragment end and a combinatorial adaptor mixture for the other fragment end thereby permitting amplification of a fragment containing known and unknown sequences, such as intron regions and flanking sequences beyond viral junctions.

The method is applicable to various targets including previously "unclonable" regions from genomic DNA, since there is no need to clone such fragments to obtain useful DNA sequence. Also, large fragments can be directly cleaved and isolated from complex genomes for subsequent analysis using the method. Also, intron sequences, the sequences flanking viral integrants, can be isolated and sequenced, as can terminal fragments from YAC, BAC, P1, plasmid or cosmid clones. The method can also be used to generate STS-like probes at rare-cutter restriction sites. Also, it will be possible to excise fragments surrounding regions of ambiguous sequence for further sequencing using the method.

In a method embodying the present invention, a population of fragments is generated from a nucleic acid sample by cleaving the sample with a Class II restriction enzyme. The identity of the Class II restriction enzyme is not critical, except to the extent that the sequence of the terminal overhang must be known, for preparing suitable adaptors. A comprehensive list of restriction endonucleases, including Class II enzymes, in Robert and Macelis, Nucleic Acids Research 26: 338–350 (1998); see also http://www.neb.com/REBASE on the world wide web. When selecting a restriction enzyme and designing the respective adaptors for use with that enzyme for restriction mapping or isolation of "sequence-ready" fragments, it is advantageous, but not essential, to minimize the differences in the composition of the recognition site by forming an overhang whose 4 bases are G, A, T and C. Any of about 50 known Class II 6-cutters (including isoschizomers) generate 3' or 5' overhangs whose 4 bases are G, A, T and C. The available enzymes include, but are not limited to, BamHI, HindIII, AvrII, ApaLI, KpnI, SphI, NsiI, and SacI. Among these enzymes, only the outermost base remaining after cleavage will vary in composition. The outermost base makes only a small and almost inconsequential contribution to the $T_m$ for adaptor-fragment annealing. This facilitates the ligation protocol, but is not to be considered essential to the invention. This design parameter also facilitates the method by helping to confine discrimination analysis to the base composition of the indexer sequences. In addition to Class II enzymes that generate four base overhangs, other enzymes that may be used effectively in the method are those that cleave palindromic sequences in opposite polarity, those that leave either blunt ends or different length overhangs (e.g., not 4-base overhangs), and those that leave base compositions other than A, G, T, and C.

After cleavage, one or more pairs of partially single-stranded indexing adaptors are hybridized under standard annealing conditions to the termini of one or more fragments generated by the enzyme cleavage. Each fragment can hybridize to a single pair of adaptors. As noted above, the sequence that complements the restriction recognition sequence can include an universal mismatch to improve discrimination between adaptor indexing sequences that are perfectly-matched and imperfectly-matched to the fragment indexing sequences. Bona fide amplification occurs when adaptors containing perfectly-matched indexing sequences are hybridized, thus there is advantage to favoring the ability of such sequences to hybridize. Hybridization should be sufficiently strong to permit subsequent ligation of fragment termini to a pair of adaptors.

After hybridization, the gap between the primer strand and the overhanging strand of the restriction fragment is closed by treating the structure with DNA ligase under standard conditions (see FIG. 1, right side), thereby joining the overhanging strand to the primer strand. T4 ligase (NEB), thermostable Ampligase (Epicentre Technologies) ligase enzymes are suitable and have been used successfully at temperatures up to 50° C. Other ligases may also be used. Suitable ligation conditions are typical of those used in the art. The result of this step is to introduce an end-specific PCR primer (or other desired sequence) onto each end of each fragment. The primer is attached only to fragments bearing a suitable indexing sequence.

Note that during hybridization the single-stranded portion of the adaptor hybridizes to its complementary sequence on the overhang strand and displaces the fragment indexing sequence (and any residual bases of the recognition site) on the opposite strand. In the special case of a 5' terminal overhanging fragment (shown in FIG. 1), the invading strand is not covalently joined to the restriction fragment. Thus, before amplification can proceed, the displaced strand is extended from its 3'-mend by polymerase in the first thermal cycle to regenerate a template complementary to the PCR primer. This extension step is not required if the termini have 3' overhangs (FIG. 2).

Fragments can be amplified using standard PCR reactions such as those described in the Example. In the preferred embodiment, one set of PCR conditions is suitable to amplify fragments of most sizes, although it may be necessary in certain cases to adjust the PCR conditions in accordance with the abilities of one skilled in the art to amplify a particular fragment. PCR protocols can be varied to accommodate particular sequences and primers. One skilled in the art will appreciate that certain modifications to the PCR protocols may be required to amplify particular fragments. Such modifications may include varying primer length, adjusting magnesium concentration, adjusting thermal cycle time, adjusting the annealing temperature and the like. It is necessary to add additional primer before amplifying. One skilled in the art will also appreciate, for example, that so-called long distance PCR conditions can be employed to amplify fragments greater than about 3 kb, although success under such conditions cannot be assured, as such protocols are still under development by the art.

Occasional false amplifications may be observed if a particular indexing sequence forms a more stable mismatch when hybridizing with the restriction fragment. However, one having ordinary skill can determine hybridization conditions under which such mismatches are not observed and do not give rise to amplification products.

In another aspect, the invention is also a system for combinatorial indexing. Combinatorial indexing is advantageously employed when seeking to separately amplify restriction fragments where the index sequence of each fragment terminus is not known. It will be appreciated that by providing every adaptor specific to both ends, all fragments generated by enzyme cleavage can be amplified, even without a priori knowledge of the sequence. In the method described above, by contrast, each fragment terminus has an indexing sequence selected from one of the possible indexing sequences (e.g., 1 of 256 possible 4-base-long indexing sequences). The unique combination of indexing sequences corresponding to the termini of an unknown fragment is one of 65,536 possible pairwise combinations of 256 left-end-specific indexing sequences and 256 right-end-specific indexing sequences.

Such a large array of possible combinations is methodologically impractical (even if automated), but would be necessary to recover all possible restriction fragments that could be generated from total digestion of a larger DNA. Even if automated, the handling of such a large array would be formidable. However, the size of the array can be reduced to 256 simply by providing in each reaction a single unique left or right end-specific adaptor along with a degenerate mixture of 256 adaptors corresponding to the second fragment end. Such mixtures are referred to herein as a "combinatorial adaptor" or a "C-adaptor." The C-adaptor mixture can be made in a single oligodeoxynucleotide synthesis process by providing all 4 nucleotides (A, G, C, T) at each adaptor indexing sequence position.

Reducing base-pairing specificity provides a way to control the number of possibilities, by combining adaptors into sets or by substituting modified bases that can pair with more than one base, or both. For instance, Py- and Pu-specific bases would have a 1 in 2 probability of pairing with each base in a random sequence, whereas any of A, C, G and T have a 1 in 4 possibility. Consequently, for n=2, for example, using any of A, C, G or T for position 1 and either Py or Pu for position 2 produces only 8 possibilities rather than 16. Likewise, for n=3, using Py or Pu in place of A, C, G or T for any one of the three positions provides 32 instead of 64 "sequences." The ability to control the number of indexing sequences in this way may be used to reduce the number of reactions and separations needed to index a given polynucleotide population.

The specificity at each position of an indexing sequence may be provided by A, C, G, T or modified bases. Reduced specificity may be provided by mixing indexing sequences or by synthesizing oligonucleotides with two or more bases in one or positions of the indexing sequences. Thus, N can be provided by mixing indexing sequence having each of A, C, G and T at the given position of N in the indexing sequence, or it can be provided by synthesizing an oligonucleotide with a mixture of A, C, G and T at the given position for N. N-specific positions can also be provided using modified bases (such as those described elsewhere herein).

A PCR reaction would yield an amplified fragment only when it contains both the end-specific indexing sequence as well as to one of the indexing sequences in the combinatorial adaptor. In 256 separate ligation/PCR reactions, the probability is that each reaction amplifies a single, sequence-ready restriction fragment. Although the invention is practiced by providing an adaptor specific to each end when 2-strand direct sequencing of the PCR products is desired, the invention can also be practiced by providing a single primer for both ends. The invention can also be practiced using a single adaptor, if PCR amplification is not desired. For example, a restriction fragment and a primer strand tagged with a reporter molecule can be annealed to a surface-bound invading strand, without subsequent ligation. The restriction fragment will anneal to the invading strand where there is correspondence between the adaptor- and fragment indexing sequences. The primer strand will also anneal to the invading strand. After annealing, unbound restriction fragments can be washed away. Interstrand base stacking interactions between the tagged primer strand and the restriction fragment will keep the primer strand annealed only where the fragment corresponds to the invading strand indexing sequence. This can facilitate specific detection of restriction fragments of interest. When used in this manner, the invention provides a method for ordering fragments in a clone.

To map the order of fragments, several independent arrays are analyzed as described using adaptors specific for different restriction enzymes and then the product of each array can be cross-digested with the enzymes of the other digestions. The products of those cross-digestions can be separated by electrophoresis and a standard restriction map can be produced for any nucleic acid fragment.

Ligation-mediated indexing using class-II enzymes can be applied to RNA fingerprinting in a way similar to that described for class-IIS enzymes (Kato, K. *NAR,* 24:394–395 (1996), incorporated herein by reference). A particular application in this regard would be for functional identification of genes by differential cDNA display. Kato and others proposed that an indexing approach could offer several advantages over the more commonly used "arbitrarily primed PCR" (Liang, P. and Pardee, A. B. *Science,* 257:967–971 (1992), incorporated herein by reference) for this purpose, including (a) obtaining more coding regions, (b) allowing lower redundancy, and (c) detecting rare messages more efficiently.

An important aspect of such a fingerprinting application is the ability to adequately resolve the fragments generated. For example, differentiated or neoplastic somatic cells have a messenger RNA complexity on the order of $20 \times 10^6$. Using a pair of 4-cutter restriction enzymes to digest cDNA, fragments are obtained that should, on average, be <200 bp in size. A given message will be represented by numerous non-overlapping fragments specifically amplified using adaptors with 4-nucleotide indexing sequences. The fingerprint of the 256 fragment subclasses generated can be well resolved on a polyacrylamide gel.

The order of the fragments for a given message can be determined either by (a) restriction mapping and/or sequencing the clone(s) from an appropriate cDNA library that cross-hybridize to the amplified fragments, or (b) amplifying the cDNA using the identified message-specific indexing adaptors in conjunction with primers which can access the 5'- and/or 3'-end of the message, and then restriction mapping and/or sequencing. As examples, the 5'-end of an mRNA can be located after preparing the cDNA using CapFinder technology (Clontech); the 3'-end of an mRNA can be accessed using oligo-dT primers as described by Liang and Pardee or oligo-dT coupled with a different or universal primer.

Single-enzyme strategies could also be used to obtain RNA fingerprints using indexers for class-II enzymes. Indexing can be confined to one of the cleaving enzymes if the second cleaving enzyme generates a constant, defined end. These strategies would target either the 5'-proximal or 3'-proximal restriction fragments of the cDNA. The cDNA could be cut with a single 4-cutter, ligated to the indexing adaptors containing a universal primer, and then PCR amplified by using either a CapFinder or oligo-dT associated primer. These approaches would yield less complex fingerprints than the double-enzyme approach, but would be biased toward detecting fewer coding regions and more untranslated regions (UTRs). However, UTRs represent excellent signatures for identifying unique messages.

Different strategies could be adopted to reduce array size and, therefore, sample handling. One strategy could utilize the combinatorial adaptors. Instead of using 256 single-end adaptors, adaptors could be pooled in several combinatorial mixtures which represent subclasses of the complete library (e.g. 4 pools×64; 16 pools×16, etc.). (A pooled subclass could also be synthesized as a degenerate oligo). The complexity of the banding pattern (per pool) will decrease as the number of pools increases. In another strategy, 3-nucleotide indexing sequences could be utilized. The size of a 3-nucleotide indexing sequence library would be 64. However, because trinucleotide frequencies are higher than tetranucleotide frequencies in a given genome, a more complex banding pattern is expected.

Another application for the method is genetic profiling, including DNA fingerprinting and RNA fingerprinting. A particularly useful DNA fingerprinting application would be detecting restriction fragment length polymorphisms. These RFLPs detect polymorphic sequences distributed throughout a genome and serve as useful markers for genetic linkage mapping.

Traditional RFLP analysis required hybridizing probes of known sequence to genomic DNA digested with various restriction enzymes. However, newer methods do not require any prior probe characterizations and can be applied to the fingerprinting of genomes of any complexity. These newer methods include random amplified polymorphic DNA (RAPD), DNA amplification fingerprinting (DAF), arbitrarily-primed PCR (AP-PCR), and amplified fragment length polymorphism (AFLP). In each of these methods, except AFLP, random genomic DNA fragments are amplified using by arbitrarily selected primers to generate fragment patterns for any DNA without prior knowledge of its sequence. AFLP (Vos, P. et al., N.A.R. 21:4407–4414 (1995)) resembles RFLP (Bostein, D. et al., Am. J. Hum. Genet. 32: 314–331), except insofar as restriction fragments are detected by PCR rather than Southern hybridization. Also, AFLP displays the presence or absence of fragments rather than their size differences. The adaptors that are ligated to the digested DNA in AFLP analysis include sets of generic PCR primers, thereby permitting the sequences which reside adjacent to the restriction sites to be queried. In AFLP, fingerprints of varying complexity can be obtained by adjusting the enzymes and primer sets employed.

AFLP can also be used for RNA fingerprinting to detect and monitor differential gene expression, starting with different double-stranded cDNA samples for a given comparative analysis (Money, T., et al. N.A.R. 24:2616–2617). Regardless of the source of DNA, however, a major disadvantage of this method is that it requires many variations in adaptor and/or PCR primer designs. This, in turn, demands that PCR conditions be optimized for each selected set of primers. Therefore, the AFLP technique is not highly amenable to formatting for streamlined multi-sample processing.

In the present invention, as in the AFLP method, fragments are queried at sequences located next to their sites. In the case of the present invention, however, an adaptor invading strand, rather than PCR primers, is used to interrogate those sequences. The adaptors can contain combinations or permutations of indexing sequences that anneal by strand-displacement to their corresponding polynucleotides. Indexing adaptors of the present invention can contain one primer sequence (pair) for amplifying the polynucleotide after the adaptor is ligated. Therefore, only one set of PCR conditions need be found for all fragments amplified, without regard to the enzyme or indexing sequences employed. Furthermore, the indexing specificity is relatively insensitive to changes in temperature, time, and ligase concentration conditions used in ligating the adaptors to the polynucleotides (results not shown). This is not unexpected since it is known that the annealing reaction during branch migration at the termini of fragments is very rapid and efficient (Quartin, R. S., et al., Biochemistry 28:8676–8682).

Taken together, these advantages mean that no variations in adaptor design or PCR conditions is intrinsically necessary, unlike in AFLP, making the method highly amenable automation and high throughput.

Genetic profiling using the present invention can be carried out using a variety of strategies, for both DNA and RNA fingerprinting. For RFLP analysis, profiles would be expected to show only the presence of new fragments or the absence of fragments resulting from mutations or sequence variations in a restriction fragment and/or an indexing sequence. The fragments created to score RFLPs would be generated using restriction enzymes that cut at frequencies amenable to PCR amplification and display by gel electrophoresis.

An RFLP strategy is chosen based on the complexity of the genomic DNA interrogated as well as the desired complexity of the fingerprint. As in the AFLP method, important variables include the character of class-II enzymes used (e.g., 4-cutter, 6-cutter) and the indexing sequencing length (e.g., 2, 3, or 4 nucleotides). For both RNA and DNA profiling, a given approach could utilize mixtures of strand-displacing adaptors and sticky-end adaptors, such as is used in an RNA fingerprinting approach for displaying differentially-expressed sequences that represent full length messages (see Examples). Alternatively, a single enzyme-adaptor set could be ligated to bring in only one PCR primer, the other being provided by a known sequence located elsewhere in the restriction fragment. This approach was used for the gene expression profiling of restriction fragments derived from the 3'-ends of mRNA in a manner resembling that described by Prashar and Weismann (U.S. Pat. No. 5,712,126, incorporated herein by reference in its entirety; see also PNAS USA 93: 659–663 (1996) and see Examples).

Unlike the widely used arbitrarily primed PCR method (Perucho, M. et al., Methods in Enzymol. 254: 275 (1995) and Liang, Methods in Enzymol. 254:304 (1995), the present invention is a form of "ligation-mediated PCR" that more efficiently detects low-abundance messages by significantly reducing the redundancy of amplified products. This is so because arbitrarily selected primers randomly amplify cDNA sequences in their entirety whereas in a ligation-mediated approach, a single pair of primers (brought in by adaptors) amplify specific portions of a message.

Adaptor primer sequences can serve least four purposes: (1) amplifying by PCR to generate profiles, (2) re-amplifying specific bands by PCR for isolating and subcloning, (3) re-amplifying specific bands for use as a direct sequencing template, and (4) generating DNA or RNA probes by PCR or by in vitro transcription, respectively. A variety of strategies can be employed for designing adaptor primer sequences. For PCR applications, the primer sequences are preferably designed such that their Tm's closely match one another, and so that the primer lengths accommodate the type of PCR reaction employed. Longer sequences may be desired, for example, to enable two-step thermal cycling, touchdown PCR, or long-distance PCR conditions. In certain cases, some sequences, such as the T7, T3, and SP6 promoter sequences, could be used for all four applications.

It may be desirable to have more than one primer sequence per adaptor, to accommodate a custom designed utility for more than one function. Resulting increases in adaptor size are not expected to significantly change the efficiency of ligation to the restriction fragments. Using primer sequences built into the adaptors, fragments isolated from fingerprints of genomic DNA or mRNA can be re-amplified and sequenced to serve as sources of genetic mapping probes or "expressed sequence tags" (EST), respectively. For DNA profiling, it may be advantageous to first perform a subtractive technique to reduce complexity, such as representational difference analysis (RDA) (Lisitsyn, N. et al., Science 259: 946–951 (1993) or "RFLP-substraction" (Rosenberg, M. et al., PNAS USA 91:6113–6117 (1994)). For RNA profiling, it may also be advantageous to first perform a subtractive technique to enrich for differentially expressed genes (for example, see Ariazi, e. and Gould, M. J. Biol. Chem., 271:29286–29294 (1996).

A targeted amplification strategy similar to that employed by U.S. Pat. No. 5,712,126 (Prashar and Weissman), incorporated herein by reference in its entirety, can also be used to amplify 3'-end restriction fragments of cDNAs to generate "fingerprints" or "expression profiles" from which bands can be recovered for sequence analysis and EST production. These fragments contain mostly untranslated sequences, which can serve as unique identifiers for messenger RNAs. These sequences are also useful for creating and searching EST databases.

By using strand-displacement adaptors in conjunction with enzymes that cut relatively frequently (e.g., 4-cutter class-II enzymes), the present invention will achieve significantly greater gene coverage than can be obtained with the Prashar and Weissman technology, which typically employs 6-cutter class-II enzymes. While U.S. Pat. No. 5,712,126 can require up to 55 6-cutters to obtain >95% gene coverage for 3'-fragments up to 400 bp in size, it is expected that >99.9% gene coverage can be obtained using only four 4-cutters in combination with tetranucleotide indexing sequences.

The strategy to generate expression profiles and ESTs in this manner is as follows:

(1) make double-stranded CDNA from total RNA or polyA+RNA using anchored oligo-dT/heel sequence;
(2) digest cDNA with a 4-cutter to produce polynucleotide fragments;
(3) ligate fragments to strand-displacement adaptor containing restriction site and indexing sequence;
(4) PCR amplify fragments using primers complementary to adaptor and anchored heel sequence, where one primer is distinguishable, e.g., includes a radiolabel, fluorescent dye label, or infrared dye label;
(5) separate the amplification products, e.g., on a denaturing polyacrylamide gel;
(6) detect the distinguishable products by, for example, autoradiography (for radioisotopic labeling), fluorimaging (for fluorescent dye labelling) or IR-imaging (for infrared dye labelling);
(7) excise bands of interest (with optional re-amplification step), and determine their nucleic acid sequences; and
(8) search databases and analyze sequences.

Genes that are differentially expressed can be profiled and recovered by using the above strategy on samples representing different cellular states such as (a) normal vs. diseased, (b) infected vs. uninfected, (c) developing vs. adult, (d) drug treated vs. untreated, and the like. Profiles are preferably displayed by running PCR products side-by-side on a denaturing polyacrylamide gel to readily observe fragments that represent genes of unchanged or altered expression. The profiling aspect of the invention can be advantageously employed in a search for novel pharmaceuticals that, for example, promote or inhibit mRNA expression by cells in a particular state. In particular, characteristic reference, average or diagnostic profiles can be established for sets of cells that exhibit differential mRNA expression.

The most stable linkages between adaptors and fragments will likely be obtained using restriction endonucleases that generate the longest possible overhangs (Weinstock, supra). In the case of 4-cutters, these would be tetranucleotide overhangs such as those generated by Sau3AI (DpnII) and Tsp509 I for 5'-overhangs, and Tai I and Cha I for 3'-overhangs.

EXAMPLES
Amplification

The feasibility of the specific amplification method described herein was tested using $N^6$-methyladenine-free bacteriophage λ DNA (48502 base pairs, New England Biolabs, Beverly, MA) as the model amplicon system and BclI, a 6-cutter, as the model Class II restriction endonuclease. Enzyme digestions were performed in the supplier's buffer at 37° C. for two hours with 20 U of BclI in a volume of 100 μl. BclI cuts the λ genome eight times, producing nine fragments that share the same 5'-overhang sequence, 5'-GATC. BclI was chosen because of the broad range of fragment sizes that the enzyme generates: 517, 560, 1576, 2684, 4459, 4623, 6330, 8844, and 18909 base pairs. The terminal fragments are 560 and 8844 base pairs. The terminal fragments include a BclI cut site at one end and the genome terminus at the other. Unique oligonucleotide primers were used to amplify the terminal λ fragments.

Since the entire nucleic acid sequence of the λ genome is known, adaptors were produced containing only the required adaptor indexing sequences. In the adaptors, the primer strand was either an M13 sequencing primer or M13 reverse sequencing primer, depending upon which end of the fragment it was specific for. Terminal primers were provided for the terminal fragments. The invading strand comprised, in 5' to 3' order, a 4-base-long indexing sequence, a 5-base-long sequence complementary to the BclI recognition site, and a portion fully and perfectly complementary to the primer strand. The primer strand and the invading strand were prepared by conventional oligonucleotide synthesis, were purified on Sep-Pak C18 cartridges and were annealed at a concentration of 12.8 μM of each primer in 50 mM tris-HCl, pH 7.8 at 85° C. The oligonucleotides were allowed to anneal by slow cooling to room temperature.

The end-specific indexing sequences used to amplify particular λ BclI fragments are shown in FIG. 3A (SEQ ID NO:1 through (SEQ ID NO:18). The end-specific adaptors that corresponded to the left (L) and right (R) ends of the fragments used the −21M13 (forward) and M13RevP (reverse) universal primer sequences, respectively. For each end, the primer strand is shown once and each partially-complementary end-specific invading strand is shown. The indexing sequences specific to each fragment end are shown in bold and the BclI site that remains after cleavage is underlined.

Once the adaptors were prepared, the BclI fragments were individually amplified from the total BclI digest as follows:

(a) 5 μg of $N^6$-methyladenine-free λ DNA (New England Biolabs, Beverly, Mass.) was digested at 37° C. or 2 hours with 20 units of BclI in a volume of 100 μl using the manufacturer's (NEB) buffer;

(b) 15 ng of digested λ DNA were combined with left and right adaptor pairs corresponding to a particular restriction fragment in NEB 1×ligase buffer for 5 minutes at 40° C. (each ligation contained 25 pmols of single end adaptor pairs, in equal amounts. For the right end of the genome, λ-specific primer CGTAACCTGTCGGAT-CAC (SEQ ID NO:21) was used. To amplify the left end of the genome (8848L), λ-specific oligonucleotide CGCGGGTTTTCGCTATTT (SEQ ID NO:22) was used);

(c) 800 units of NEB T4 DNA ligase were added and the reactions were incubated for 20 minutes at 40° C. and were stopped by heating to 65° C. for 15 minutes;

(d) 1.5 ng of λ DNA were transferred to 100 μl PCR reactions. All PCR reactions were performed with the XL-PCR kit (Perkin-Elmer, Applied Biosystems Division, Foster City, Calif.), using 2 μl (4 units) of rTth DNA polymerase. The PCR reactions included 1.1 mM magnesium acetate (1 mM $MgCl_2$ carried over from the ligase reaction), except the amplification of the 4,459 base pair BclI fragment from λ DNA which included 1.65 μl of magnesium acetate to obtain robust and specific amplification from its combinatorial adaptor. The specific products could also be obtained using 0.55 mM magnesium acetate. All PCR reactions contained 10 pmols of appropriate primer oligonucleotides. PCR was performed in the PTC-200 DNA engine (MJ Research, Watertown, Mass.) using the following thermal cycling profile: 95° C. for 1.5 minutes followed by 30 cycles of 94° C. for 40 seconds, 55° C. for 40 seconds, 72° C. for 5 minutes. Treatment with 3'-to-5' exonuclease activity of Vent polymerase was important for increasing the yields of the PCR products obtained with rTth polymerase.

(e) 20 μl were loaded on 0.8% agarose gels containing 0.5 μg per μl ethidium bromide. Specific bands were observed upon electrophoresis.

No reactant removal or product purifications were required between steps, making the overall procedure amenable to automation. In some conditions, it may be advantageous, but not absolutely necessary, to purify fragment-bound adaptors away from unligated adaptors or fragments. A solid-phase purification step can be included. However, the need for such a solid-phase purification has not been observed.

When the appropriate left/right adaptor pairs or terminal/left or right adaptor pairs were used, eight of the nine BclI fragments of λ DNA were selectively and specifically amplified. Under the conditions described, specific amplification of the 18909 base pair fragment was not observed, although the fragment was observed with additional non-specific fragments, including the 6.3K, 4.6K, 4.4K, 2.6K and 1.5K lambda fragments. These fragments were amplified at least in part because a longer polymerase extension time was required just to detect the 18909 base fragment. In this case, fragments arising from rare non-specific ligation events are amplified to a greater extent. However, when 3-nitropyrrole was incorporated into the restriction site of the adaptor, all of the extra bands were eliminated. The suppression of the nonspecific fragments was optimal when the 3-nitropyrrole was positioned in the middle of the 9-nucleotide protruding single-strand region of each of the 18K-specific adaptors.

It is possible to achieve good discrimination among the adaptor pairs tested. Where non-targeted restriction fragments were co-amplified along with the desired product, the extra amplification can be explained by homology in some indexing sequence positions and the potential for stable mis-match duplex formation in other indexing sequence positions. Few non-specific products that did not co-migrate with the restriction fragments were observed.

Combinatorial Indexing

To demonstrate the utility of the method employing combinatorial adaptors, two sets of combinatorial primers were prepared, as is shown in FIG. 3B. The "combo-FP" adaptor included the −21M13 (SEQ ID NO:1) primer hybridized to the indicated C-adaptors (SEQ ID NO:19 and SEQ ID NO:20), where N at each position indicated in the adaptor represents a population of all four nucleotides at that position. Thus, each mixture of combinatorial adaptors included 256 different adaptors. Likewise, the "combo-RP" adaptor set included the M13revP primer hybridized to the indicated set of invading strands where N is all four nucleotides at each position.

To amplify various fragments of BclI-cut λ DNA, the following amounts of the indicated end-specific adaptors (or primers in the case of the terminal fragments) were combined with the indicated amounts of combo-FP or combo-RP mixtures.

TABLE I

| Fragment to be amplified (bp) | Right adaptors (pmol) | Left adaptors (pmol) | Combo-FP mix (pmol) | Combo-RP mix (pmol) |
|---|---|---|---|---|
| 517 | | | | |
| 560 | 10 (560R*) | — | 0.0025 | — |
| 1576 | 25 | — | 0.5 | — |
| 2684 | 25 | — | 0.25 | — |
| 4459 | 25 | — | 25 | — |
| 4623 | 25 pmol | — | 25 | — |
| 6330 | — | — | — | — |
| 8848 | — | 10 (8848L*) | — | 0.0025 |

*Primer only (in PCR reaction)

Specific amplification of fragments having the expected fragment length were observed by polyacrylamide gel electrophoresis, thus indicating that desired fragments can be amplified by providing an adaptor specific for one end of a desired fragment and a mixture of adaptors containing an adaptor specific for the indexing sequence at the other end of the fragment. It is of note that no purification was required prior to PCR amplification to remove ligation reactants or intermediate products.

Specific fragment amplification was driven predominantly by the end-specific adaptor ligated at one end. That is because when the end-specific adaptor and C-adaptors are provided at equimolar amounts, the relative concentration of a single indexing sequence in the combinatorial mixture is only 1/256 as great as the amount of the end-specific adaptor, thereby favoring more efficient ligation of the more prevalent adaptor.

In additional tests, it was shown that specific fragments were amplified from the total BclI-λ DNA digest over a range of asymmetric end-specific:C-adaptor concentration ratios. The ratios of end-specific adaptors:C-adaptors was varied from 1:1 to 100:1. An additional hundred-fold dilution of the combinatorial adaptor yielded the most specific λ terminal fragment amplifications.

Amplification from Genomic Polynucleotides

To demonstrate that specific amplification can be accomplished in the presence of a more complex genome, *E. coli* DNA containing λc1857Sam7dam⁻ lysogen (NEB) was used as the amplification target. This more complex genome (4.7 Mb) has 1,604 BclI sites, 200 times as may as λ DNA. Despite this increase in target complexity, λ BclI fragments could still be specifically amplified using the adaptors tested.

Eighteen μg of the λ lysogen DNA was digested with BclI. Twenty five pmol (each) of left and right adaptors were used to amplify the 517, 1576, and 2684 bp fragments. Subsequent dilutions and reactions were performed as described above for λ DNA.

Although the concept has been demonstrated using known DNA, it is equally applicable to unknown DNA targets excised directly from the genome. Using the method, a DNA fragment that maps between two STS markers can be obtained. At least two 6-cutter arrays will be used in conjunction with combinatorial indexing to obtain a complete restriction map of the selected fragment and the production of contigs. PCR amplification products produced from each array will be subjected to agarose gel electrophoresis to acquire fragment length information.

RNA Fingerprinting

RNA fingerprinting using adaptors for class-II enzymes was tested for the differential display of cDNA from rat mammary carcinomas, untreated or treated with perillyl alcohol (PA) which is a monoterpene used for chemoprevention and chemotherapy (Crowell, P. L. and Gould, M. N. *Crit. Rev. Oncog.*, 5L:1–22 (1994), incorporated herein by reference). cDNA from treated and untreated tumors (at half-regression) was prepared by and according to Ariazi, E. and Gould, M. (*J. Biol. Chem.*, 271:29286–29294 (1996), incorporated herein by reference).

In a preliminary study, DpnII (GATC) and NlaIII (CATG) were used as the cleavage enzymes. DpnII provides indexing sequences next to its 5'-overhang and NlaIII provides a defined 3'-overhang for a cohesive end adaptor. Because a DpnII site will not anneal with an NlaIII site, fragment chimeras are minimized and primer-dimer formation during PCR is eliminated. As is shown in FIG. 4, the NlaIII adaptor contains the M13 reverse primer sequence and the DpnII adaptors contain the M13 forward primer sequence. For this study, four 4-nucleotide indexing sequences were used (FIG. 4, SEQ ID NO:1 and SEQ ID NO:23 through SEQ ID NO:28). The adaptors were designed such that the chance of forming stable mismatches was minimized according to the observations of Ebel et al., *Biochemistry* 31:12083–12086 (1992), incorporated herein by reference.

A suitable protocol for generating fingerprints was as follows. Note that if the enzyme cleavage buffers are compatible with one another, the cleavages can be accomplished in a double digestion.

(1) digest 0.5 μg cDNA (−/+PA treatment) with NlaIII;
(2) clean-up*, elute in water;
(3) join NlaIII adaptor (25 pmol) with 800U T4 DNA ligase at 37° C.;
(4) clean-up, elute in water;
(5) digest with Dpn II;
(6) clean-up, elute in water;
(7) split cDNA four ways (125 ng ea.) and join Dpn II adaptors (25 pmol) with 800U T4 DNA ligase at 40° C.;
(8) use Klentaq (Advantage cDNA PCR kit, Clontech, Palo Alto, Calif.) to amplify 5 ng of ligated DNA using 25 pmol ea. of the −21M13 and M13rev primers;
(9) run aliquots on 5% polyacrylamide electrophoresis gels; stain with Sybr Green I (Molecular Probes, Eugene, Oreg.) to separate and visualize a characteristic pattern for amplified fragments;
(10) visualize by UV transillumination or laser scanning (Fluorimager 575, Molecular Dynamics, Sunnyvale, Calif.)

* each clean-up step used Qiaquick spin column (Qiagen, Chatsworth, Calif.) to remove enzymes, buffers and/or unligated adaptors.

For the two 4-cutter approach, an average expected number of amplified products per gel lane (i.e. per indexer) was estimated by (20×106/512)/256, or approximately 150, assuming a perfectly random distribution of sites and a perfectly random sequence of nucleotides in the total cDNA. However, because the sequences are not random in nature, fragment size range varies. For the 4 indexing adaptors tested, the size of the observed amplified fragments ranged from about 50 bp to about 300–500 bp. The bands were well separated and indicated a quasi-random distribution of restriction sites useful for fingerprinting and probe isolations. The fingerprints observed were highly reproducible for a given set of thermal cycling parameters and yielded differentially expressed bands indicating both up-regulation and down-regulation after PA treatment (confirmed by varying the amount of template in the PCR). The sensitivity of the assay was high, detecting as little as 2–3 fold changes in the levels of some differentially expressed bands. However, to distinguish truly differentially expressed bands from false positives, it would typically be necessary to re-amplify a band and use it as a probe against Northern blots.

Amplification of mRNA/cDNA 3' ends

The 3'-end-targeted amplification strategy employing the adaptors of the present invention was tested on Sau3AI digested cDNA prepared from resting and activated human (Jurkat) T-lymphocytes. Activated Jurkat T cells are known to contain highly elevated levels of interleukin-2 (IL-2) mRNA. A 40-mer oligonucleotide (CAGGGTAGACGACGCTACGC($T_{18}$)AT; SEQ ID NO:32) was used as an anchor primer for cDNA synthesis and PCR primer in the fragment amplification step. In SEQ ID NO:32, CAGGGTAGACGACGCTACGC is the "heel" sequence, T18 is an 18-mer oligo-dT portion that can anneal to the poly-A tail of messenger RNAs, and AT is the dinucleotide anchor sequence. AT was chosen because its complement is contained in interleukin-2 (IL-2) mRNA. The 3'-proximal Sau3AI site of IL-2 cDNA is located 142 bp from the poly-A. The indexing sequence adjacent to the 3'-proximal Sau3AI site is AAAA on the anti-sense strand of the restriction fragment.

An adaptor was prepared by annealing an 18-mer oligonucleotide (TGTAAAACGACGGCCAGT; SEQ ID NO:1) corresponding to the M13 forward primer sequence and a 26-mer invading strand that contained the M13 sequence complementary to the forward primer sequence, the Sau3AI tetranucleotide overhang and the AAAA indexing sequence (SEQ ID NO:37). FIG. 5 depicts the strand displacement structure formed by ligating the adaptor to the IL-2 Sau3AI fragment as well as the primers used for PCR. FIG. S also shows eight indexing sequences tested (IS-I through 1S-8) besides that for IL-2 (IS-9) (SEQ ID NO:23 through SEQ ID NO:26 and SEQ ID NO:33 through SEQ ID NO:37, respectively from top to bottom in FIG. 5). An IL-2 specific fragment of 200 bp is amplified (26 bp+40 bp+142 bp−8 bp, where 8 bp is the overlap between adaptor and fragment).

Total RNA was prepared, cDNA was synthesized, adaptors were formed, polynucleotides were digested, ligated and amplified using Ampligase Gold (ABI-Perkin Elmer) as described in U.S. Pat. No. 5,712,126, except that the restriction enzyme and adaptors of Prashar and Weissman were substituted by Sau3AI and the indexing adaptors, respectively. For detecting the amplified fragments, the M13 forward primer was end-labeled with $^{32}$p using polynucleotide kinase according to a standard protocol. Amplified restriction fragments were separated by electrophoresis on an 8M urea-6% polyacrylamide denaturing gel, and an autoradiograph was obtained by exposing the dried gel to X-ray film for approximately 16 hours.

The nine fingerprints observed on the autoradiograph are non-overlapping (i.e., share no apparent bands) and contain fragments representing differentially expressed genes. Base-pairing specificity within the indexing sequence was determined by re-amplifying, subcloning and sequencing five fragments excised from each of the nine fingerprints. No base pair mismatches were observed, indicating 100% specificity for 40 fragments that were targeted (5 fragments did not yield readable sequence in this experiment). Less than 20% non-specificity was observed in the systemic background, that is only in non-targeted cDNA fragments revealed only in the fragment library subclones. Close to the number of expected fragments (see table below) were observed, strongly suggesting that gene coverage efficiency is high under the ligation and PCR reaction employed.

Furthermore, the fingerprints were consistently reproducible with respect to band patterns and signals, and identical fingerprints were observed by fluorescent imaging when a tetramethylrhodamine (TAMRA)-labeled M13 primer was substituted for the $^{32}$P-labeled M13 primer. From sixty nonredundant sequences analyzed from the nine adaptor profiles, 34 matches with human genes were found in the Genbank-primate database (5 differentially expressed, including IL-2), 22 matches in the gb-EST database were found (2 differentially expressed), and four fragments showed no matches (1 differentially expressed) and represent novel genes. In the preceding example, simple, well-resolved fingerprints (15–20 fragments per lane) are generated by using a dinucleotide anchor primer in combination with tetranucleotide indexing sequences. Although this combination yields close to the theoretical number of expected 3'-fragments (~10), the number of ligation reactions to achieved 99% gene coverage is extremely large, and for 4 enzymes is [256 adaptors]×[12 $N_1N_2$-oligo(dT) primers]×4=10,240. This would be a formidable task even if automated.

TABLE 2

Parsing Reduction Strategies

| Strategy | 5'-end IS length | set | 3'-end | # expected frags/lane | # ligations (4-enzs) |
|---|---|---|---|---|---|
| I | 4 | 256 | N1N2 (×12) | 10 | 10,240 |
| II | | | N1 (×3) | 40 | 2,560 |
| III | | | N0 | 120 | 853 |
| IV | 3 | 64 | N1N2 | 40 | 3,072 |
| V | | | N1 | 160 | 768 |
| VI | | | N0 | 480 | 256 |

Table 2 shows six parsing reduction strategies that could be employed to reduce the number of reactions to a manageable size. These strategies do not consider the use of "combinatorial mixtures" of base-pairing specifity, which could further reduce the total number of reactions required. In Table 2, parsing reduction can be targeted to one or both ends of the restriction fragments by reducing the number of indexing bases (5'-end) from four to three in the ligation step, or oligo-dT anchor bases (3'-end) from two ($N_1N_2$) to one ($N_1$) to zero ($N_0$) in the PCR step. Table 2 shows the reduction in the number of reactions for the six different 5'/3' combinations, with a proportional increase in the number of expected fragments per lane. In the case of $N_0$, only the "heel" portion (see FIG. 5) need provide the sequence for a 3' PCR primer. These latter numbers were statistically derived using 4-cutter sites of sequences from the Expressed Gene Anatomy Database (EGAD) of The Institute for Genomic Research (www.tigr.org) and projected for mRNA complexity of 15,000 unique transcripts. Only 3'-proximal fragments up to 400 bp in size were considered in the statistical analysis since this represents the upper limit of gel resolution. This size, on the other hand, is significantly greater than the mean size of fragments generated by 4-cutters and therefore only a small fraction will be lost by gel exclusion.

From Table 2, it can be seen that strategies III&V are likely candidates for parsing reduction since they yield manageable numbers of both reactions and resolvable fragments. Strategies I, II and IV produce too many reactions, while strategy VI produces a large number of fragments that cannot be readily resolved.

The present invention is not intended to be limited to the preceding embodiments, but rather to encompass all such variations and modifications as come within the scope of the appended claims.

We claim:

1. A method for indexing polynucleotides, comprising the steps of:
    (A) combining under base-pairing conditions:
        (i) one or more distinguishable sets of indexing adaptors, each adaptor comprising a sequence for amplification and at least one terminus having a single-stranded region characterized by, in non-overlapping order inward from the end: (a) an indexing sequence n bases long and (b) a sequence characteristic of cleavage by a Class II restriction endonuclease, wherein n is an integer and wherein further each set of adaptors comprises one or more indexing sequences, and
        (ii) one or more corresponding polynucleotides, each of which comprises at least one terminus characterized by, in non-overlapping order inward from the end: (a) a region having a sequence characteristic of cleavage by a Class II restriction endonuclease and (b) a double-stranded region having on one strand a sequence that base-pairs with an indexing sequence of an adaptor and on the other strand a sequence complementary thereto;
    (B) base-pairing at least one adaptor terminus and at least one corresponding polynucleotide terminus to form at least one strand-displaced structure wherein the indexing sequence of the single-stranded region of the adaptor terminus is base-paired with the sequence that base-pairs with an indexing sequence of the terminus of the corresponding polynucleotide, and the complementary sequence on the other strand of the polynucleotide terminus is displaced from base-pairing thereto;
    (C) for each adaptor set, amplifying the corresponding polynucleotides that form strand-displaced structures using the sequence for amplification; and
    (D) distinguishing the amplified corresponding polynucleotides thereby indexing the polynucleotides by their base-pairing to the distinguishable sets of adaptors.

2. A method according to claim 1, wherein n is 1 to 4.

3. A method according to claim 2 wherein n is 2, 3 or 4.

4. A method according to claim 1, wherein the indexing adaptors in all the sets of adaptors together comprise all possible sequences of A, T, G and C n bases long.

5. A method according to claim 1, wherein the sequence for amplification is selected from a group consisting of a PCR primer, a T3 promoter, a T7 promoter, an SP6 promoter, and a sequence complementary to any of the same.

6. A method according to claim 1, wherein the amplification is an exponential amplification.

7. A method according to claim 1, further comprising the step of ligating, in a strand-displaced structure, the end of the adaptor strand comprising the indexing sequence to the end of the abutting strand of the double-stranded region of the corresponding polynucleotide.

8. A method according to claim 7, wherein strand-displaced structures are formed at both ends of at least one corresponding polynucleotide.

9. A method according to claim 8, wherein the sequence for amplification is a PCR primer.

10. A method according to claim 1, wherein the sequence characteristic of cleavage by a Class II restriction endonuclease has a 3'-terminated single-stranded region.

11. A method according to claim 1, wherein the sequence characteristic of cleavage by a Class II restriction endonuclease has a 5'-terminated single-stranded region.

12. A method according to claim 1,,, wherein the sequence characteristic of cleavage by a Class II restriction endonuclease has a blunt end.

13. A method for characterizing a population of polynucleotides, comprising the steps of:
    (A) combining under base-pairing conditions:
        (i) one or more distinguishable sets of indexing adaptors, each adaptor comprising a sequence for amplification and at least one terminus having a single-stranded region characterized by, in non-overlapping order inward from the end: (a) an indexing sequence n bases long and (b) a sequence characteristic of cleavage by a Class II restriction endonuclease, wherein n is an integer and wherein further each set of adaptors comprises one or more indexing sequences, and
        (ii) a population of polynucleotides that includes one or more corresponding polynucleotides, each of which comprises at least one terminus characterized by, in non-overlapping order inward from the end: (a) a region having a sequence characteristic of cleavage by a Class II restriction endonuclease and (b) a double-stranded region having on one strand a sequence that base-pairs with an indexing sequence of an adaptor and on the other strand a sequence complementary thereto;
    (B) base-pairing at least one adaptor terminus to at least one corresponding polynucleotide terminus to form at least one strand-displaced structure wherein the indexing sequence of the single-stranded region of the adaptor terminus is base-paired with the sequence that base-pairs with an indexing sequence of the terminus of the corresponding polynucleotide, and the complementary sequence on the other strand of the polynucleotide terminus is displaced from base-pairing thereto;

(C) for each adaptor set, amplifying corresponding polynucleotides that form strand-displaced structures using the sequence for amplification;

(D) determining one or more amplified corresponding polynucleotides or the absence thereof; and (E) characterizing the population of polynucleotides by the amplified corresponding polynucleotides that form strand-displaced structures using the sequence for amplification, or the absence thereof.

14. A method according to claim 13, wherein n is 1 to 5.

15. A method according to claim 13, wherein the population is a population of cDNAs or other polynucleotides representative of mRNAs.

16. A method according to claim 15, wherein the characterization is indicative of gene expression in a sample from which the population was derived.

17. A method according to claim 13, wherein the population is a population of genomic DNAs or polynucleotides representative of genomic DNAs.

18. A method according to claim 17, wherein the characterization comprises characterizing mutations or the absence thereof in: (a) the sequence characteristic of cleavage by a Class II restriction endonuclease; (b) the indexing sequence or both (a) and (b) of one or more corresponding polynucleotides in the population.

19. A method according to claim 18, wherein the absence or presence of a mutation thus characterized in one or more corresponding polynucleotides is diagnostic of a potential to develop one or more diseases, or of one or more diseases.

20. A method according to claim 13, further comprising the step of ligating, in a strand-displaced structure, the end of the adaptor-strand comprising the indexing sequence to the end of the abutting strand of the double-stranded region of the corresponding polynucleotide.

21. A method according to claim 20 wherein strand-displaced structures are formed at both ends of at least one corresponding polynucleotide.

22. A method according to claim 21, wherein the sequence for amplification is a PCR primer.

23. A method according to claim 22, further comprising the step of amplifying by PCR corresponding polynucleotides having adaptor strands ligated to each terminus, using the sequences for amplification either as a primer or as a primer binding site.

24. A method according to claim 13, further comprising, for at least one adaptor set, resolving from one another at least two corresponding polynucleotides that form strand-displaced structures.

25. A method according to claim 24, wherein the population is a population of cDNAs or other polynucleotides representative of mRNAs in a sample, the size and the quantity of the separated corresponding polynucleotides is determined, each separated corresponding polynucleotide is identified by the indexing sequence and the Class II restriction endonuclease characteristic sequence of the adaptor set with which it formed a strand-displaced structure and by its size, and the quantities of the thus identified corresponding polynucleotides for at least two adaptor sets provides a profile of gene expression in the source from which the cDNA was derived.

26. A method according to claim 25, wherein corresponding polynucleotides for at least one set of adaptors are resolved by size by electrophoresis.

27. A method according to claim 25, wherein the sequences characteristic of a Class II restriction endonuclease and the indexing sequences of the adaptor sets together subdivide the cDNAs or other polynucleotides representative of the mRNAs into sets of corresponding polynucleotides in each of which corresponding polynucleotides can be individually differentiated by electrophoresis.

28. A method for comparing mRNA in two or more samples, comprising the steps of claim 25 to generate a profile of gene expression of a first sample and, independently, a profile of gene expression in a second sample and comparing the profiles of the first and second samples.

29. A method according to claim 13, wherein the sequence for amplification is selected from a group consisting of a PCR primer, a T3 promoter, a T7 promoter, an SP6 promoter, and a sequence complementary to same.

* * * * *

UNITED STATES PATENT AND TRADEMARK OFFICE
CERTIFICATE OF CORRECTION

| | |
|---|---|
| PATENT NO. | : 6,280,948 B1 |
| APPLICATION NO. | : 09/380786 |
| DATED | : August 28, 2001 |
| INVENTOR(S) | : Richard A. Guilfoyle and Zhen Guo |

It is certified that error appears in the above-identified patent and that said Letters Patent is hereby corrected as shown below:

Column 1, line 7;

Please add the following statement regarding Government Support:

This invention was made with United States government support awarded by the following agencies: DOE, Grant No. DE-FG02-91ER61122, Case No. S-89,006; and NIH, Grant No. HG00321. The United States has certain rights in this invention.

Signed and Sealed this

Thirty-first Day of March, 2009

JOHN DOLL
*Acting Director of the United States Patent and Trademark Office*

SEQUENCE LISTING

<160> NUMBER OF SEQ ID NOS: 37

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:   -21M13
       forward primer

<400> SEQUENCE: 1
tgtaaaacga cggccagt                                                    18

```
<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: end
      specific adaptor (517L)

<400> SEQUENCE: 2
ctggtgatca ctggccgtcg ttttaca                                              27

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: end
      specific adaptor (560L)

<400> SEQUENCE: 3
atggtgatca ctggccgtcg ttttaca                                              27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: end
      specific adaptor (1567L)

<400> SEQUENCE: 4
atagtgatca ctggccgtcg ttttaca                                              27

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: end
      specific adaptor (2684L)

<400> SEQUENCE: 5
ctgatgatca ctggccgtcg ttttaca                                              27

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:  end
      specific adaptor (4459L)

<400> SEQUENCE: 6
cgggtgatca ctggccgtcg ttttaca                                              27

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: end
      specific adaptor (4623L)

<400> SEQUENCE: 7
gaactgatca ctggccgtcg ttttaca                                              27
```

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: end
      specific adaptor (6330L)

<400> SEQUENCE: 8
aaactgatca ctggccgtcg ttttaca                                              27

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: end
      specific adaptor (18909L)

<400> SEQUENCE: 9
cggctgatca ctggccgtcg ttttaca                                              27

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence:  M13RevP
      reverse primer

<400> SEQUENCE: 10
caggaaacag ctatgacc                                                        18

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: end
      specific adaptor (517R)

<400> SEQUENCE: 11
gaagtgatcg gtcatagctg tttcctg                                              27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: end
      specific adaptor (1576R)

<400> SEQUENCE: 12
tgactgatcg gtcatagctg tttcctg                                              27

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: end
      specific adaptor (2684R)

<400> SEQUENCE: 13
aggctgatcg gtcatagctg tttcctg                                              27

<210> SEQ ID NO 14

```
<211> LENGTH: 27
<212> TYPE: DNA
<213> ORGANISM: Artificial Sequence
<220> FEATURE:
<223> OTHER INFORMATION: Description of Artificial Sequence: end
      specific adaptor (4459R)

<400> SEQUENCE: 14
gaggtgatcg gtcatagctg tttcctg                                              27

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: end
      specific adaptor (4623R)

<400> SEQUENCE: 15
tccttgatcg gtcatagctg tttcctg                                              27

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: end
      specific adaptor (6330R)

<400> SEQUENCE: 16
cagttgatcg gtcatagctg tttcctg                                              27

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: end
      specific adaptor (8848R)

<400> SEQUENCE: 17
gatttgatcg gtcatagctg tttcctg                                              27

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: end
      specific adaptor (18909R)

<400> SEQUENCE: 18
gtggtgatcg gtcatagctg tttcctg                                              27

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence:
      combinatorial adaptor invading strand for forward primer
<221> NAME/KEY: misc_feature
<222> LOCATION: (1)..(4)
<223> OTHER INFORMATION: Each nucleotide base may be either a, t, c, or
      g.

<400> SEQUENCE: 19
nnnntgatca ctggccgtcg ttttaca                                              27
```

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence:
      combinatorial adaptor invading strand for reverse
      primer
<221> NAME/KEY: misc_feature
<222> LOCATION: (1)..(4)
<223> OTHER INFORMATION: Each nucleotide base may be either a, t, c, or
      g.

<400> SEQUENCE: 20
nnnntgatcg gtcatagctg tttcctg                27

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence:   lambda
      terminal primer (right end)

<400> SEQUENCE: 21
cgtaacctgt cggatcac                18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence:   lambda
      primer (left end)

<400> SEQUENCE: 22
cgcgggtttt cgctattt                18

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: end
      specific adaptor

<400> SEQUENCE: 23
ccaggatcac tggccgtcgt tttaca                26

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: end
      specific adaptor

<400> SEQUENCE: 24
cagcgatcac tggccgtcgt tttaca                26

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: end
      specific adaptor

```
<400> SEQUENCE: 25
agccgatcac tggccgtcgt tttaca                                                26

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: end
      specific adaptor

<400> SEQUENCE: 26
agaggatcac tggccgtcgt tttaca                                                26

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: M13 reverse
      primer with NlaIII adaptor

<400> SEQUENCE: 27
caggaaacag ctatgaccca tg                                                    22

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence:   adaptor
      strand

<400> SEQUENCE: 28
ggtcatagct gtttcctg                                                         18

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence:   invading
      and primer strand for 3'-overhang adaptor
<221> NAME/KEY: misc_feature
<222> LOCATION: (24)..(27)
<223> OTHER INFORMATION: Each nucleotide base may be either a, t, c, or
      g.

<400> SEQUENCE: 29
tgtaaaacga cggccagtac gtcnnnn                                               27

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence:
      oligonucleotide complementary to M13 forward
      primer

<400> SEQUENCE: 30
actggccgtc gttttaca                                                         18

<210> SEQ ID NO 31
<211> LENGTH: 27
<212> TYPE: DNA
```

```
<213> ORGANISM: Artificial Sequence
<220> FEATURE:
<223> OTHER INFORMATION: Description of Artificial Sequence:
      oligonucleotide complementary to M13 forward
      primer after ligation to 3' overhang restriction
      fragment end
<221> NAME/KEY: misc_feature
<222> LOCATION: (1)..(4)
<223> OTHER INFORMATION: Each nucleotide base may be either a, t, c, or
      g.

<400> SEQUENCE: 31
nnnngacgta ctggccgtcg ttttaca                                              27

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence:
      oligonucleotide anchor primer for cDNA synthesis
      and PCR primer in fragment amplification step

<400> SEQUENCE: 32
cagggtagac gacgctacgc tttttttttt ttttttttat                                40

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: end
      specific adaptor

<400> SEQUENCE: 33
tcaggatcac tggccgtcgt tttaca                                               26

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: end
      specific adaptor

<400> SEQUENCE: 34
ctgagatcac tggccgtcgt tttaca                                               26

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: end
      specific adaptor

<400> SEQUENCE: 35
atatgatcac tggccgtcgt tttaca                                               26

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: end
      specific adaptor

<400> SEQUENCE: 36
```

-continued

```
tatagatcac tggccgtcgt tttaca                                        26

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: end
      specific adaptor

<400> SEQUENCE: 37
aaaagatcac tggccgtcgt tttaca                                        26
```